United States Patent [19]

Chasar et al.

[11] Patent Number: 4,515,733

[45] Date of Patent: May 7, 1985

[54] METHOD FOR MAKING 1,3,5,2,4,6-TRIOXATRIPHOSPHORINANES

[75] Inventors: Dwight W. Chasar, Northfield; Perry D. Matheny, Doylestown, both of Ohio

[73] Assignee: The B. F. Goodrich Co., Akron, Ohio

[21] Appl. No.: 548,910

[22] Filed: Nov. 7, 1983

[51] Int. Cl.$^3$ ................................. C07F 9/15
[52] U.S. Cl. ........................ 260/988; 260/927 R
[58] Field of Search ............................. 260/988

[56] References Cited

U.S. PATENT DOCUMENTS 4,404,150 9/1983 Tsnekawa et al. ............... 260/988
4,473,509 9/1984 Grosse et al. ..................... 260/988

Primary Examiner—Anton H. Sutto
Attorney, Agent, or Firm—J. Hughes Powell, Jr; Alan A. Csontos

[57] ABSTRACT

An improved process for preparing 2,4,6-tris(substituted phenoxy)-1,3,5,2,4,6-trioxatriphosphorinanes is realized when the appropriate substituted-phenylphosphorodichloridite is reacted with water in the presence of a trialkyl amine wherein the alkyl groups contain 4 to 8 carbon atoms in acetone as the sole solvent, to provide the desired 2,4,6-tris(substituted phenoxy)-1,3,5,2,4,6-trioxatriphosphorinanes in increased yields and of a higher purity.

6 Claims, No Drawings

METHOD FOR MAKING 1,3,5,2,4,6-TRIOXATRIPHOSPHORINANES

BACKGROUND OF THE INVENTION

Novel stabilizers for organic materials subject to degradation, 2,4,6-tris(substituted phenoxy)-1,3,5,2,4,6-trioxatriphosphorinanes that form effective stabilizer combinations with hindered phenol compounds, particularly hydroxyphenylalkyleneyl isocyanurates, have been prepared by the reaction of substituted phenylphosphorodichloridites, water and triethylamine in tetrahydrofuran. At least one other solvent is required to isolate and purify the product for use. A less complex single solvent process that also provides improved yields of product of a higher purity is desired.

SUMMARY OF THE INVENTION

An improved process for preparing 2,4,6-tris(substituted phenoxy)-1,3,5,2,4,6-trioxatriphosphorinanes is realized when the appropriate substituted-phenylphosphorodichloridite is reacted with water in the presence of a trialkyl amine wherein the alkyl groups contain 4 to 8 carbon atoms, in acetone as the sole solvent, to provide the desired 2,4,6-tris(substituted phenoxy)-1,3,5,2,4,6-trioxatriphosphorinanes at increased yields and of a higher purity.

DETAILED DESCRIPTION

Use of this novel process provides a number of advantages over other processes and methods that have been used to make 2,4,6-tris(substituted phenoxy)-1,3,5,2,4,6-trioxatriphosphorinanes. Improved yields of desired product are obtained. The 2,4,6-tris(substituted phenoxy)-1,3,5,2,4,6-trioxatriphosphorinane is more readily separated from the amine hydrochloride byproduct that forms during the reaction. The 2,4,6-tris(substituted phenoxy)-1,3,5,2,4,6-trioxatriphosphorinane is in a purer state and substantially free of an undesired acid byproduct formed when lower trialkyl amines such as triethylamine are used. A less complex process comprising less handling and fewer processing steps is realized for a savings of energy and labor costs. For example, only one solvent is required that is less expensive than solvents previously used. This avoids costly solvent recovery, storage, recycling, etc., and eliminates the possibility of solvent contamination when more than one solvent is used.

The 2,4,6-tris(substituted phenoxy)-1,3,5,2,4,6-trioxatriphosphorinanes may be represented by the general formula (1)

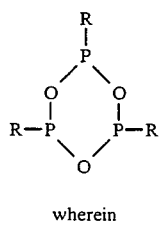

wherein

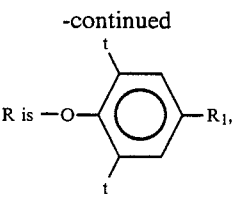

or (2),

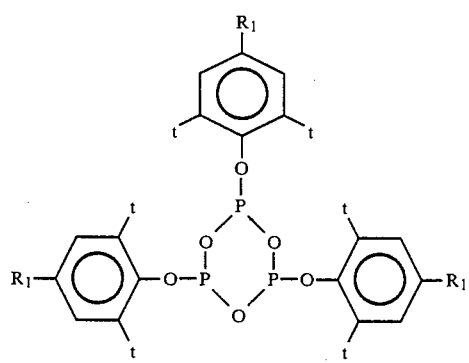

wherein t is t-butyl or t-pentyl and $R_1$ is hydrogen, primary, secondary, and tertiary alkyl radicals containing 1 to 9 carbon atoms such as methyl, ethyl, isopropyl, n-butyl, t-butyl, amyl, t-amyl, hexyl, heptyl, 2-methylhexyl, 2-ethylhexyl, octyl, isooctyl, and the like; cycloalkyl radicals containing 3 to 6 carbon atoms; halogen; C≡N; alkoxy radicals containing 1 to 8 carbon atoms, such as methoxy, ethoxy, butoxy and the like; phenyl, $COOR_2$ wherein $R_2$ is an alkyl radical containing 1 to 18 carbon atoms; —$CH_2CH_2COOR_3$ wherein $R_3$ is an alkyl radical containing 1 to 18 carbon atoms, and —$C(CH_3)_2CON(R_4)_2$ wherein $R_4$ is an alkyl group containing 1 to 9 carbon atoms.

Preferably t is t-butyl and $R_1$ is hydrogen, an alkyl radical containing 1 to 4 carbon atoms, alkoxy radicals containing 1 to 4 carbon atoms, —$COOR_2$, —$CH_2CH_2COOR_3$, and —$C(CH_3)_2CON(R_4)_2$ radicals wherein $R_2$, $R_3$ and $R_4$ are alkyl radicals containing 1 to 4 carbon atoms.

Typical 2,4,6-tris(substituted phenoxy)-1,3,5,2,4,6-trioxatriphosphorinanes are: 2,4,6-tris(2,6-di-t-butylphenoxy)-1,3,5,2,4,6-trioxatriphosphorinane and 2,4,6-tris(2,6-di-t-butyl-4-substituted phenoxy)-1,3,5,2,4,6-trioxatriphosphorinanes wherein the radicals substituted at the 4-position are those described above. Typical compounds are 2,4,6-tris(2,6-di-t-butyl-4-methylphenoxy)-1,3,5,2,4,6-trioxatriphosphorinane, 2,4,6-tris(2,6-di-t-butyl-4-ethylphenoxy)-1,3,5,2,4,6-trioxatriphosphorinane, 2,4,6-tris(2,6-di-t-butyl-4-propylphenoxy)-1,3,5,2,4,6-trioxatriphosphorinane, 2,4,6-tris(2,6-di-t-butyl-4-isopropylphenoxy)-1,3,5,2,4,6-trioxatriphosphorinane, 2,4,6-tris(2,6,-di-t-butyl-4-n-butylphenoxy)-1,3,5,2,4,6-trioxatriphosphorinane, 2,4,6-tris(2,6-di-t-butyl-4-isoamylphenoxy)-1,3,5,2,4,6-trioxatriphosphorinane, 2,4,6-tris(2,6-di-t-butyl-4-methoxyphenoxy)-1,3,5,2,4,6-trioxatriphosphorinane, 2,4,6-tris(2,6-di-t-butyl-4-ethoxyphenoxy)-1,3,5,2,4,6-trioxatriphosphorinane, 2,4,6-tris(2,6-di-t-butyl-4-carbomethoxyphenoxy)-1,3,5,2,4,6-trioxatriphosphorinane, 2,4,6-tris(2,4,6-tri-t-butylphenoxy)-1,3,5,2,4,6-trioxatriphosphorinane, 2,4,6-tris[2,6-di-t-butyl-4-(2-carboethoxyethyl)phenoxy]-1,3,5,2,4,6-trioxatriphosphorinane, 2,4,6-tris[2,6-di-t-butyl-4-(1-methyl-1-diethylcarbamoylethyl)phenoxy]-1,3,5,2,4,6-trioxatriphosphorinane, and 2,4,6-tris[2,6-di-t-butyl-4-(2-carbooctadecyloxyethyl)phenoxy]-1,3,5,2,4,6-trioxatriphosphorinane.

To make the 2,4,6-tris(substituted phenoxy)-1,3,5,2,4,6-trioxatriphosphorinanes, a substituted phenylphosphorodichloridite is reacted with water and a tertiary alkyl amine in acetone at low temperatures for short periods of time; and the resulting 2,4,6-tris(substituted phenoxy)-1,3,5,2,4,6-trioxatriphosphorinane is readily obtained by filtering the reaction mixture, to separate the 1,3,5,2,4,6-trioxatriphosphorinane and washing the crude product with acetone.

Substituted phenylphosphorodichloridites used in the process of the invention include those substituted at the 2,6- and 2,4,6-positions on the phenyl group. The 2- and 6-positions are substituted with the t-butyl or t-pentyl groups, while the 4-position may be substituted with the alkyl, alkoxy, carboxyester, and like radicals as set forth for the

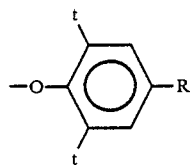

radical above. These substituted phenylphosphorodichloridites are readily prepared by reacting the alkylphenol with a molar excess of $PCl_3$ to form the substituted phenylphosphorodichloridite that may be isolated by distillation. Procedures for preparing the substituted phenylphosphorodichloridite are found in U.S. Pat. No. 3,271,481. One of the advantages of this invention is that isolation of the substituted phenylphosphorodichloridite by distillation is not required, and the substituted phenylphosphorodichloridite may be prepared in situ and used per se in the improved method of this invention.

Typical substituted phenylphosphorodichloridite reactants include 2,6-di-t-butyl-4-methylphenylphosphorodichloridite, 2,6-di-t-butyl-4-ethylphenylphosphorodichloridite, 2,6-di-t-butyl-4-propylphenylphosphorodichloridite, 2,4,6-tri-t-butylphenylphosphorodichloride, 2,6-di-t-butyl-4-t-butylphenylphosphorodichloridite, 2,6-di-t-butyl-4-methoxyphenylphosphorodichloridite, 2,6-di-t-butyl-4-ethoxyphenylphosphorodichloridite, 2,6-di-t-butyl-4-carbomethoxyphenylphosphorodichloridite, 2,6-di-t-butylphenylphosphorodichlororidite, 2,6-di-t-butyl-4-(1-methyl-1-diethylcarbamoylethyl)phenylphosphorodichloridite, 2,6-di-t-butyl-4-(2-carboethoxyethyl)phenylphosphorodichloridite, 2,6-di-t-butyl-4-nonylphenylphosphorodichloridite, and the like.

The amines are trialkylamines wherein the alkyl radicals contain 4 to 8 carbon atoms, including for example, tributylamine, tripentylamine, triisopentylamine, trihexylamine, triheptylamine, trioctylamine, and the like. The preferred tributylamine has a specific gravity of 0.775±0.005 at 20° C., less than 0.1 weight percent water and a color value measured at 420 nanometers of less than 0.25 absorbance units.

The molar ratios of the reactants normally used are about one mole of the substituted phenylphosphorodichloridite, one mole of water and two moles of the amine. While these proportions may be varied within a range of about 1 to 0.8 to 2.0 of water and 0.5 to 10 of amine, better yields are obtained when about a 1:1:2 mol ratio is observed. Of course, an excess of any reactant may be used but good yields will depend on there being at least about one mol of water and one mole of amine present. The amount of acetone used will vary from 3.5 to 25 moles based on one mole of substituted phenylphosphorodichloridite used.

The reaction is quite rapid and usually is conducted at about 25° C. to control the reaction rate, although the reaction temperature may vary from about 0° C. to 50° C. The reaction products prepared in accordance with this novel process normally need only be filtered as the reaction product has precipitated from the solvent, is separated by filtration, washed with acetone, and dried.

The structures of the 2,4,6-tris(substituted phenoxy)-1,3,5,2,4,6-trioxatriphosphorinanes are confirmed by infrared and nuclear magnetic resonance spectra. Molecular weights were determined and confirmed by field desorption mass spectra (FD/MS) and fast atom bombardment mass spectra (FAB/MS). In some cases elemental analysis for carbon, hydrogen and phosphorus was done and the amounts found were consistent with the formula of the material.

The following Example is a typical preparation of the phosphorinanes by a process used prior to this invention.

EXAMPLE I 2,4,6-tris(2,6-di-t-butyl-4-methylphenoxy)-1,3,5,2,4,6-trioxatriphosphorinane 6.0 grams (0.019 mol) of 2,6-di-t-butyl-4-methylphenylphosphorodichloridite and 3.78 grams (0.037 mol) of triethylamine were dissolved in 100 ml of tetrahydrofuran, and the solution was cooled to 0°–5° C. 0.34 gram (0.019 mol) of water was added to the solution and the mixture was stirred for 0.5 hour. The resulting reaction mixture was filtered and the filtrate was evaporated to a dry white glass. The dry product was stirred twice with saturated aqueous sodium bicarbonate solution for ten minutes, filtered, washed with water and air dried to provide the white solid (4.04 grams) 84% of theoretical yield. After washing in methanol, the solid had a mp 170°–184° C., and the melt was cloudy and had an orange color. It was determined by infra red analysis that this phosphorinane was contaminated with an acidic byproduct derived from the phosphorodichloridite. Calculated for $C_{15}H_{23}O_2P$: C, 67.65; H, 8.71; P,11/63. Found: C, 67.7; H, 8.68; P, 11.53. FD/MS: 799 (actual 798.96), 266

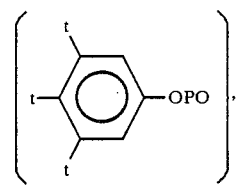

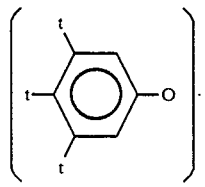

FAB/MS: 799. IR (Nujol) 950, 930 (P-O), 848, 820 cm$^{-1}$. $^1$H NMR(CDCl$_3$): 1.35 (S,18H), 1.47 (S,36H), 2.26 (S, 3H), 2.29 (S, 6H), 7.07 (S, 2H), 7.11 (S, 4H). $^{31}$P NMR (CDCl$_3$): 120.0 (d,J=10, 2P), 127.9 (t,J=10, 1P).

EXAMPLE II 2,4,6-tris(2,6-di-t-butyl-4-methylphenoxy)-1,3,5,2,4,6-trioxatriphosphorinane 6.31 grams (0.06 mole) of triethylamine was charged to a reactor. 10.0 grams (0.032 mol) of 2,6-di-t-butyl-4-methylphenylphosphorodichloridite dissolved in 110 ml of acetone was then added to the reactor and the solution was adjusted to 20°–25° C. 0.56 gram (0.037 mol) of water in 15 ml of acetone was added to the solution in the reactor and the mixture was stirred for 0.5 hour. The resulting reaction mixture contained a white solid precipitate of both the 2,4,6-tris(2,6-di-t-butyl-4-methylphenoxy)-1,3,5-2,4,6-trioxatriphosphorinanes and triethylamine hydrochloride. The reaction product was filtered, the recovered solid product was washed with water to wash out the triethylamine hydrochloride by-product, and air dried to provide the white solid, 45% yield, melting point 181°–185° C. The melt was cloudy and had an orange color. The presence of the undesired acidic by-product obtained when triethylamine is used is determined by infra red.

EXAMPLE III p 5.77 grams (0.031 mol) of tributylamine was charged to a reaction vessel equipped with stirring, heating and cooling means. 5 grams (0.016 mol) of 2,6-di-t-butyl-4-methylphenylphosphorodichloridite dissolved in 65 ml of acetone was added to the reactor. With the solution at a temperature of 20°–25° C., 0.28 grams (0.016 mol) of water dissolved in 10 ml of acetone was slowly added, with stirring, to the reaction mixture and stirred for 0.5 hour. The 2,4,6-tris(2,6-di-t-butyl-4-methylphenoxy)-1,3,5,2,4,6-trioxatriphosphorinane crystallized from the reaction mixture and was removed by filtration. The tributylamine hydrochloride by-product was soluble in the acetone, as compared to Example II where the triethylamine hydrochloride precipitated out with the phosphorinane and had to be removed in an additional step. The white solid was washed with acetone to yield 3.33 grams of 2,4,6-tris(2,6-di-t-butyl-4-methylphenoxy)-1,3,5,2,4,6-trioxatriphosphorinane for a yield of 80%. This product was free of tributylamine hydrochloride. The melting point was 177°–181° C., the melt was clear and free of acidic by-product impurity. This is to be compared to Example I, where the use of triethylamine rather than tributylamine resulted in the acid byproduct.

EXAMPLE IV

Example III above was repeated with the difference that methyl ethyl ketone was used as the solvent rather than acetone. In this Example, the 2,4,6-tris(2,6-di-t-butyl-4-methylphenoxy)-1,3,5,2,4,6-trioxatriphosphorinane did not crystallize or precipitate from the reaction mixture but was dissolved in the methyl ethyl ketone. The reaction solution had to be heated to strip off the methyl ethyl ketone. After heating the reaction to dryness, the residue was stirred for 0.5 hour in 75 ml of acetonitrile to separate the insoluble phosphorinane from the soluble tributylamine hydrochloride. The resulting white solid was removed by filtration and washed with acetonitrile. 2.62 grams of 2,4,6-tris(2,6-di-t-butyl-4-methylphenoxy)-1,3,5,2,4,6-trioxatriphosphorinane was obtained for a yield of only 63 percent and a melting point of 181°–185° C. This Example and Example I, demonstrate the undesirable results obtained with solvents other than acetone. The melt was cloudy and yellow colored.

When Example III is repeated with 2,4,6-tri-t-butylphenylphosphorodichloridite and/or with other higher alkyl amines, as tripentylamine, triisopentylamine, trihexylamine, triheptylamine and trioctylamine, yields of about 80% are readily obtained. On a cost and handling basis, tributylamine is preferred.

To further demonstrate the advantages of this invention using acetone as the solvent and tributylamine as the hydrogen chloride acceptor, the preparation of the substituted phenylphosphorodichloridite may be done in situ and used per se in the phosphorinane formation as shown in Example V.

EXAMPLE V 2,6-di-t-butyl-4-methylphenol (40 g, 0.18 moles) and tributylamine (100.9 g, 0.55 moles) were charged to a reaction vessel and phosphorus trichloride (24.9 g, 0.18 moles) was added. After heating this mixture for 1 hour at 110° C., the mixture was cooled to 25° C. and 100 ml acetone was added. Water (3.27 g, 0.18 moles) dissolved in 25 ml of acetone was dropped in slowly to maintain the reaction temperature below 30° C. A cooling bath may be used if needed. After addition was complete, the mixture was stirred for 0.5 hour. The solid was removed by filtration, washed with acetone and was air dried to give an 82% yield of 2,4,6-tris(2,6-di-t-butyl-4-methylphenoxy)-1,3,5,2,4,6-trioxatriphosphorinane, melting point of 176°–181° C.

Example V was repeated using tributylamine that had a specific gravity of 0.785 and an absorbance of 0.55 unit at 420 nanometers. A reduced product yield of only 68.5% was obtained that had a melting point of 173°–182° C.

Organic materials stabilized by the 2,4,6-tris(2,6-di-t-butyl-4-methylphenoxy)-1,3,5,2,4,6-trioxatriphosphorinane prepared in accordance with this invention include both natural and synthetic polymers. For example, the phosphorinane stabilizers are useful for the stabilization of cellulosic materials; natural rubber; halogenated rubber, conjugated diene polymers like polyisoprene, polychloroprene; vinyl polymers such as poly(vinyl chloride); hompolymers and copolymers of acrylate monomers; epihalohydrin polymers; polyether-, polyester- or polyol-derived polyurethanes; acetal homopolymers and copolymers; polycarbonates; polyesters such as polyethylene terephthalate; polyamides; epoxy resins, and the like.

In addition to polymeric materials, the phosphorinane compounds may be used to stabilize a wide variety of other organic materials. Such materials include: waxes, synthetic and petroleum-derived lubricating oils and greases; animal oils such as, for example, fat, tallow, lard, codliver oil, sperm oil; vegetable oils such as castor, linseed, peanut, palm, cotton seed, and the like; fuel oil; diesel oil, gasoline and the like.

We claim:

1. A method for making 2,4,6-tris(substituted phenoxy)-1,3,5,2,4,6-trioxatriphosphorinanes comprising reacting together substituted phenylphosphorodichloridites having the formula

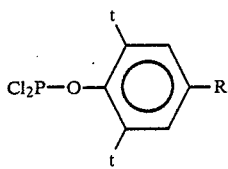

wherein t is t-butyl or t-pentyl, R is hydrogen, a primary, secondary, or tertiary alkyl radical containing 1 to 9 carbon atoms, cycloalkyl radicals containing 3 to 6 carbon atoms, a halogen radical, a cyano radical, alkoxy radicals containing 1 to 8 carbon atoms, phenyl, —$COOR_2$, —$CH_2CHO_2COOR_3$ and —$C(CH_3)_2CON(R_4)_2$ radicals wherein $R_2$ and $R_3$ are alkyl radicals containing 1 to 18 carbon atoms, and $R_4$ is an alkyl radical containing 1 to 9 carbon atoms, with water and a trialkylamine wherein the alkyl group contains 4 to 8 carbon atoms, in acetone.

2. A method of claim 1 wherein in the substituted phenylphosphorodichloridite is t-butyl and R is H or an alkyl radical containing 1 to 4 carbon atoms, an alkoxy radical containing 1 to 4 carbon atoms, —$COOR_2$, —$CH_2CH_2COOR_3$ or —$C(CH_3)_2CON(R_4)$ radicals wherein $R_2$, $R_3$ and $R_4$ are methyl or ethyl, and the ratio of reactants is about one mole of substituted phenylphosphorodichloridite to about one mole of water to about two moles of amine.

3. A method of claim 2 wherein the trialkyl amine is tributylamine.

4. A method of claim 3 wherein the substituted phenylphosphorodichloridite is 2,6-di-t-butylphenylphosphorodichloridite.

5. A method of claim 3 wherein the phosphorodichloridite is 2,6-di-t-butyl-4-methylphenylphosphorodichloridite.

6. A method of claim 3 wherein the phosphorodichloridite is 2,4,6-tri-t-butylphenylphosphorodichloridite.

* * * * *